(12) United States Patent
Tang et al.

(10) Patent No.: US 7,704,531 B2
(45) Date of Patent: Apr. 27, 2010

(54) ENHANCED EFFICACY ALUMINUM OR ALUMINUM-ZIRCONIUM ANTIPERSPIRANT SALT COMPOSITIONS CONTAINING CALCIUM SALT(S) AND BETAINE

(75) Inventors: Sheridan Tang, Bridgewater, NJ (US); Marian N. Holerca, Somerset, NJ (US); Donghui Wu, Bridgewater, NJ (US); Christine M. Popoff, Morganville, NJ (US)

(73) Assignee: Colgate-Palmolive Company, New York, NY (US)

( * ) Notice: Subject to any disclaimer, the term of this patent is extended or adjusted under 35 U.S.C. 154(b) by 331 days.

(21) Appl. No.: 11/348,499

(22) Filed: Feb. 6, 2006

(65) Prior Publication Data

US 2006/0204463 A1    Sep. 14, 2006

Related U.S. Application Data

(60) Provisional application No. 60/654,070, filed on Feb. 18, 2005.

(51) Int. Cl.
*A61Q 15/00* (2006.01)
*A61K 8/28* (2006.01)
*A61K 8/26* (2006.01)
*A61K 9/00* (2006.01)
*A61K 8/02* (2006.01)

(52) U.S. Cl. .................. 424/667; 424/65; 424/66; 424/68; 424/400; 424/401

(58) Field of Classification Search .................. 424/65, 424/66, 68, 400, 401
See application file for complete search history.

(56) References Cited

U.S. PATENT DOCUMENTS

| | | | |
|---|---|---|---|
| 2,256,505 A | 9/1941 | Thompson | |
| 2,571,030 A | 10/1951 | Thomas et al. | |
| 3,553,316 A | 1/1971 | Rubino | |
| 3,963,833 A | 6/1976 | DeSalva | |
| 3,998,788 A | 12/1976 | Rubino | |
| 4,017,599 A | 4/1977 | Rubino | |
| 4,021,536 A | 5/1977 | Rubino | |
| 4,025,615 A | 5/1977 | Rubino | |
| 4,058,597 A | 11/1977 | Passedouet et al. | |
| 4,331,609 A | 5/1982 | Orr | |
| 4,359,456 A | 11/1982 | Gosling et al. | |
| 4,435,382 A | 3/1984 | Shin et al. | |
| 4,526,780 A | 7/1985 | Marschner et al. | |
| 4,722,835 A | 2/1988 | Schamper | |
| 4,775,528 A | 10/1988 | Callaghan et al. | |
| 4,781,917 A | 11/1988 | Luebbe et al. | |
| 4,816,261 A | 3/1989 | Luebbe et al. | |
| 4,871,525 A | 10/1989 | Giovanniello et al. | |
| 5,102,656 A | 4/1992 | Kasat | |
| 5,162,378 A | 11/1992 | Guthauser | |
| 5,200,174 A | 4/1993 | Gardlik | |
| 5,225,187 A | 7/1993 | Carmody | |
| 5,250,291 A | 10/1993 | Park | |
| 5,254,230 A | 10/1993 | Joshi et al. | |
| 5,516,511 A | 5/1996 | Motley et al. | |
| 5,518,714 A | 5/1996 | Park | |
| 5,520,907 A | 5/1996 | Orofino | |
| 5,534,246 A | 7/1996 | Herb et al. | |
| 5,589,196 A | 12/1996 | Callaghan et al. | |
| 5,595,729 A | 1/1997 | Barr et al. | |
| 5,599,533 A | 2/1997 | Stepniewski et al. | |
| 5,643,558 A | 7/1997 | Provancal et al. | |
| 5,653,970 A | 8/1997 | Vermeer | |
| 5,955,065 A | 9/1999 | Thong et al. | |
| 5,997,850 A | 12/1999 | Tang et al. | |
| 6,024,945 A | 2/2000 | Parekh | |
| 6,042,816 A * | 3/2000 | Shen | 424/65 |
| 6,066,314 A | 5/2000 | Tang et al. | |
| 6,245,325 B1 | 6/2001 | Shen | |
| 6,265,364 B1 | 7/2001 | Kilpatrick-Liverman et al. | |
| 6,436,381 B1 | 8/2002 | Carrillo et al. | |
| 6,726,901 B2 | 4/2004 | Yin et al. | |
| 6,902,723 B2 | 6/2005 | Shen | |
| 6,902,724 B1 | 6/2005 | Parekh et al. | |
| 6,911,195 B2 | 6/2005 | Vu et al. | |
| 6,923,952 B2 | 8/2005 | Allen et al. | |
| 6,942,850 B2 | 9/2005 | Coe et al. | |
| 7,014,843 B2 | 3/2006 | Parekh et al. | |
| 7,105,691 B2 * | 9/2006 | Holerca et al. | 556/27 |
| 2003/0049219 A1 | 3/2003 | Lemoine et al. | |
| 2004/0091436 A1 | 5/2004 | Li et al. | |
| 2004/0109833 A1 | 6/2004 | Tang et al. | |
| 2004/0198998 A1 | 10/2004 | Holerca et al. | |
| 2004/0204601 A1 | 10/2004 | Holerca et al. | |
| 2004/0228887 A1 | 11/2004 | Champ et al. | |

(Continued)

FOREIGN PATENT DOCUMENTS

DE    26 10 225    9/1976

(Continued)

OTHER PUBLICATIONS

File History from U.S. Appl. No. 11/307,689 as of Jan. 29, 2008.
Search Report from Corresponding PCT Application No. PCT/US2006/005054 Mailed on Jul. 3, 2006.
Copending Application File History U.S. Appl. No. 11/560,677.
File History from U.S. Appl. No. 11/560,677.
File History from U.S. Appl. No. 11/161,117 (US2007/0020211) as of Feb. 10, 2009.

*Primary Examiner*—Johann R Richter
*Assistant Examiner*—Luke E Karpinski
(74) *Attorney, Agent, or Firm*—Michael F. Morgan

(57) ABSTRACT

An antiperspirant composition comprising an antiperspirant salt selected from an aluminum antiperspirant salt, an aluminum-zirconium antiperspirant salt, and a mixture thereof; a betaine component selected from betaine, betaine hydrochloride, and a mixture thereof; a calcium salt; and water.

44 Claims, No Drawings

U.S. PATENT DOCUMENTS

| | | |
|---|---|---|
| 2004/0265255 A1 | 12/2004 | Holerca et al. |
| 2005/0036967 A1 | 2/2005 | Allen et al. |
| 2005/0036968 A1 | 2/2005 | Shen |
| 2005/0036969 A1 | 2/2005 | Coe et al. |
| 2005/0100521 A1 | 5/2005 | Cropper |
| 2005/0265939 A1 | 12/2005 | Li et al. |
| 2007/0020211 A1 | 1/2007 | Li et al. |
| 2007/0110687 A1 | 5/2007 | Mattai et al. |
| 2007/0196303 A1 | 8/2007 | Li et al. |
| 2007/0286830 A1 | 12/2007 | Li et al. |

FOREIGN PATENT DOCUMENTS

| | | |
|---|---|---|
| EP | 274267 A1 | 7/1988 |
| EP | 523168 B1 | 1/1993 |
| EP | 0 653 203 | 5/1995 |
| EP | 0 499 456 | 12/1996 |
| EP | 1 005 852 | 6/2000 |
| EP | 1 005 853 | 6/2000 |
| EP | 1005852 | 6/2000 |
| EP | 1005853 | 6/2000 |
| GB | 880261 A | 10/1961 |
| GB | 2048 229 A | 12/1980 |
| WO | WO 96/19228 A1 | 6/1996 |
| WO | WO 01/39730 | 6/2001 |
| WO | WO 01/47479 | 7/2001 |
| WO | WO 2004/026295 A1 | 7/2004 |
| WO | WO 2004/089325 | 10/2004 |

* cited by examiner

ENHANCED EFFICACY ALUMINUM OR ALUMINUM-ZIRCONIUM ANTIPERSPIRANT SALT COMPOSITIONS CONTAINING CALCIUM SALT(S) AND BETAINE

CROSS-REFERENCE TO RELATED APPLICATION

The present application claims priority to U.S. Provisional Patent application Ser. No. 60/654,070, filed on Feb. 18, 2005.

BACKGROUND OF THE INVENTION

The efficacy of an antiperspirant salt can be increased, improved and/or sustained for a longer period of time by enhancing the amount of small molecules of the antiperspirant active salt. Typically, when an aluminum or aluminum-zirconium antiperspirant salt is formed, it tends to polymerize into a number of polymeric species. Each polymeric species is correlated with at least one HPLC peak (also referred to as a GPC peak in U.S. Pat. No. 6,066,314). In U.S. Pat. No. 6,066,314, FIGS. 1-6 thereof represent GPC plots of peaks 1, 2, 3, 4, 5 and 6. Peak 1 corresponds to a zirconium polymeric species with peaks 2-6 corresponding to aluminum polymeric species. The area under the curve (AUC) at the position of each peak is proportional to the amount of the corresponding polymeric species.

Without being bound by theory, it is believed that the size of the polymeric species corresponding to peaks 5 and 6 are smaller than the polymeric species corresponding to the other aluminum peaks (i.e., peaks 2-4). Again without being bound by theory, it is believed that the sequence of the peaks corresponds to the size of the corresponding aluminum polymerics so that peak 2 polymer size>peak 3 polymer size>peak 4 polymer size>peak 5 polymer size>peak 6 polymer size.

It is further believed, without being bound by theory, that the antiperspirant efficacy of a given antiperspirant is inversely proportional to the polymer size of the relevant polymeric species. Also without being bound by theory, this is believed to be true because smaller antiperspirant polymeric species can more readily occlude a pore to a degree sufficient to produce the desired antiperspirant effect. In sum, it is believed that smaller species plug-up the sweat pores more readily and more effectively than do the larger species and, therefore, antiperspirants having a higher proportion of the smaller species will be more effective.

This theory is the basis for the discussion of peak ratios described in U.S. Pat. No. 6,066,314 (assigned to the Colgate-Palmolive Co.) and U.S. Pat. No. 6,245,325 (assigned to the Gillette Company). In the '325 patent, there is a discussion of the ratio of the peak 4 AUC/peak 3 AUC. This ratio can be increased by increasing the portion of the smaller peak 4 species and/or decreasing the relative portion of the larger peak 3 species. Thereby, the efficacy of the antiperspirant can be enhanced, increased and/or maintained for a longer period of time. In effect, the effort is to improve the stability of the smaller peak 4 species over that of the larger peak 1, 2, and/or 3 species.

To ascertain whether a particular antiperspirant's efficacy has been improved, a number of ingredients may be added to the antiperspirant and then the peak 4 AUC/peak 3 AUC ratio measured by HPLC or GPC as described in the '314 patent. So, as the peak 4 AUC/peak 3 AUC ratio is increased, the proportion of the desirable smaller peak 4 species is increased relative to the less desirable larger peak 3 species.

This peak 4 AUC/peak 3 AUC ratio is also referred to herein as the peak 4/peak 3 ratio or a "first ratio." Another peak ratio, i.e., the peak 1 AUC/(peak 2 AUC+peak 3 AUC+peak 4 AUC+peak 5 AUC+peak 6 AUC) ratio is referred to herein as the "second ratio." Also, because peaks 5 and 6 often appear as a single merged peak at peak 5, this "second ratio" is also sometimes referred to as the peak 1 AUC/(peak 2 AUC+peak 3 AUC+peak 4 AUC+peak 5 AUC) ratio with the understanding that the peak 6 AUC is part of the peak 5 AUC.

Additionally, the "first ratio" is proportional to an 27al NMR peak appearing at 63.5 ppm. Thus, an increase in the "first ratio" and an increase in the intensity of the "27al NMR peak appearing at 63.5 ppm", each represent what is believed to be an increase in the amount of the peak 4 species relative to the amounts of the other polymeric species of the other 2, 3, 5 and 6 peaks. It should be born in mind that peak 1 corresponds to zirconium species and peaks 2-6 correspond to aluminum species.

While the above-noted theory is believed to be sound, such understanding is made without being bound by theory in the event that the changes measured in the "first ratio", "second ratio" and the "27al NMR peak appearing at 63.5 ppm" yield a more efficacious antiperspirant product due to some, as yet, unrecognized mechanism.

With the foregoing background being provided, there is a need to provide a more effective antiperspirant product. It is believed that a more effective antiperspirant product can be provided by increasing its "first ratio," decreasing its "second ratio," and/or increasing the intensity of the "27al NMR peak appearing at 63.5 ppm."

It is desirable to provide a more effective antiperspirant. It is also desirable to provide an antiperspirant with an increased "first ratio" and/or a decreased "second ratio." It is also desirable to provide an antiperspirant having an increased intensity of the "27al NMR peak appearing at 63.5 ppm."

SUMMARY OF THE INVENTION

An improved or more effective antiperspirant composition is provided in accordance with one embodiment of the invention. According to one embodiment, the more effective antiperspirant composition comprises:

(a) an antiperspirant salt selected from the group consisting of an aluminum antiperspirant salt, an aluminum-zirconium antiperspirant salt, and a mixture thereof;

(b) a betaine component selected from the group consisting of betaine, betaine hydrochloride, and a mixture thereof;

(c) a calcium salt; and (d) water.

Other embodiments within the scope of the present invention are also contemplated as discussed and illustrated below.

DETAILED DESCRIPTION OF EMBODIMENT(S) OF THE INVENTION

At the outset, it should be noted that this application discusses various embodiment(s) and examples in accordance with the present invention. No part of this application is intended to be construed to limit the scope of the claimed invention whether in the Background of the Invention, the Summary of the Invention, the Examples or in the Detailed Description of Embodiment(s) of the Invention. All discussions in this application are to be construed as illustrative, exemplary and non-limiting with regard to the scope of the claimed invention.

Unless expressly indicated otherwise, amount(s) of each ingredient noted in this application are provided in "% by weight" units based on the total amount of the entire antiperspirant composition recited in the claim(s).

One exemplary embodiment of the invention is the antiperspirant composition noted above in the Summary of the Invention. Each component is now discussed in order below.

Suitable examples of aluminum salts, aluminum/zirconium salts or mixtures thereof for use in connection with the claimed invention include, but are not limited to, conventional aluminum and aluminum/zirconium salts, as well as aluminum/zirconium salts complexed with a complexing agent, such as glycols, as are known in the art in the form of aluminum zirconium chlorohydrex propylene glycol complex, aluminum zirconium chlorohydrex dipropylene glycol complex, aluminum zirconium chlorohydrex tripropylene glycol complex and mixtures of any of the foregoing.

Suitable examples of zirconium salts for use in connection with the claimed invention include (but are not limited to) zirconyl hydroxychlorides, zirconyl oxychlorides, basic aluminum chlorides combined with zirconyl oxychlorides and hydroxychlorides, and organic complexes of each of basic aluminum chlorides with zirconyl oxychlorides and hydroxychlorides and mixtures of any of the foregoing. Generally, the foregoing metal antiperspirant active materials are antiperspirant active metal salts.

Suitable aluminum salts for use in conjunction with the claimed invention include, but are not limited to, aluminum chlorohydrate, aluminum dichlorohydrate, aluminum sesquichlorohydrate, aluminum chlorohydrex propylene glycol, aluminum dichlorohydrex propylene glycol, aluminum sesquichlorohydrex propylene glycol, aluminum chlorohydrex polyethylene glycol, aluminum dichlorohydrex polyethylene glycol, aluminum sesquichlorohydrex polyethylene glycol and combinations thereof. See also the '314 and '325 patents and references cited therein, each of which is incorporated herein by reference in its entirety (including the references cited therein) for all purposes.

Exemplary suitable amounts of the component (a) antiperspirant used in conjunction with the claimed invention include, but are not limited to, (1) from about 5 to about 85% (or from 5-85%), (2) from about 5 to about 78% (or from 5-78%), (3) from about 10 to about 70% (or from 10-70%), (4) from about 10 to about 60% (or from 10-60%), (5) from about 12 to about 50% (or from 12-50%), (6) from about 13 to about 40% (or from 13-40%), and (7) from about 15 to about 35% (or from 15-35%).

It should be noted that whatever the amount of the component (a) antiperspirant, the total amount of the final claimed antiperspirant composition (including any optional or other ingredients) cannot exceed 100%.

The "betaine" recited in the claims means the "betaine" of Formula I:

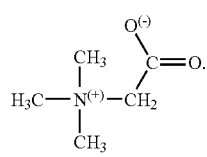

(Formula I)

In IUPAC nomenclature, betaine is 1-carboxy-N,N,N-trimethylmethanaminium hydroxide-inner salt, with alternative names including carboxymethyl-trimethyl-ammonium betaine or (carboxymethyl)trimethylammonium hydroxide-inner salt or glycine betaine or glycol betaine or glycyl betaine or trimethylglycine or trimethylglycol. For convenience here the material of Formula I ($C_5H_{11}NO_2$; Mass=117.08 amu; molecular weight=117.15; analysis as C, 51.26; H, 9.46; N, 11.96; O: 27.32) will be referred to herein as "betaine."

While betaine is sometimes incorrectly referred to as an amino acid, it is in fact a zwitterion. For purposes of this application, betaine is not considered to be an amino acid. The betaine used in this invention is a natural product found in a number of plants in the Chenopodiaceae family, and also in fish and selected legumes. Its synthetic analog can also be used. It is extracted most often from sugar beets (*Beta Vulgaris*).

Exemplary suitable amounts of the component (b) betaine used in conjunction with the claimed invention include, but are not limited to, (1) at least about 0.1% (or $\geq 0.1\%$), (2) from about 0.5 to about 40% (or from 0.5-40%), (3) from about 1.0 to about 35% (or from 1.0-35%), (4) from about 2.0 to about 30% (or from 2.0-30%), (5) from about 3.0 to about 25% (or from 3.0-25%), (6) from about 4.0 to about 20% (or from 4.0-20%), and (7) from about 4.5 to about 15% (or from 4.0-15%), and (7) from about 15 to about 35% (or from 15-35%).

It should be noted that whatever the amount of the component (b) betaine, the total amount of the final claimed antiperspirant composition (including any optional or other ingredients) cannot exceed 100%.

Suitable examples of Ca salts for use in connection with the claimed invention include, but are not limited to, calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide or mixtures thereof.

Exemplary suitable amounts of the component (c) calcium salt used in conjunction with the claimed invention include, but are not limited to, (1) at least about 0.1% (or $\geq 0.1\%$), (2) from about 0.2 to about 80% (or from 0.2-80%), (3) from about 0.3 to about 60% (or from 0.3-60%), (4) from about 0.4 to about 40% (or from 0.4-40%), (5) from about 0.45 to about 20% (or from 0.45-20%), and (6) from about 0.5 to about 10% (or from 0.5-10%).

It should be noted that whatever the amount of the component (c) calcium salt, the total amount of the final claimed antiperspirant composition (including any optional or other ingredients) cannot exceed 100%.

After any optional ingredients in the claimed antiperspirant composition of the claimed invention, water comprises the remainder thereof. It should be noted that whatever the amount of all the ingredients of the claimed composition including water (or any optional ingredients), the total amount of the final claimed antiperspirant composition cannot exceed 100%. In fact, the total of all the ingredients of the claimed composition (including any optional ingredients present) must total to 100%.

An exemplary optional component of the claimed antiperspirant composition may be one or more water soluble alcohol(s). Suitable examples of water soluble alcohol(s) for use with the claimed invention include, but are not limited to, C2-C8 alcohols, C2-C3 alcohols, ethanol, glycol (G), propylene glycol (PG), dipropylene glycol (DG), tripropylene glycol (TG) or mixtures thereof.

Exemplary suitable amounts of the optional water soluble alcohol used in conjunction with the claimed invention include, but are not limited to, (1) from about 0 to about 40% (or 0-40%), (2) from about 2 to about 35% (or from 2-35%), (3) from about 4 to about 30% (or from 4-30%), (4) from about 6 to about 25% (or from 6-25%), (5) from about 8 to about 20% (or from 8-20%), and (6) from about 10 to about 15% (or from 10-15%).

Optionally, glycine may be included in the claimed antiperspirant composition. Exemplary suitable amounts of the optional glycine used in conjunction with the claimed invention include, but are not limited to, (1) from about 0 to about 40% (or 0-40%), (2) from about 1 to about 30% (or from 1-30%), (3) from about 2 to about 20% (or from 2-2%), and (4) from about 4 to about 50% (or from 4-50%), (5) from about 6 to about 20% (or from 6-20%), and (6) from about 8 to about 10% (or from 8-10%).

Other optional ingredients such as fragrance(s), color(s), dye(s), pigment, etc. may be included in the claimed antiperspirant composition. See Handbook of Cosmetic Science and Technology, Editors—A. Bard, M. Paye and H. Maibach, Marcel Dekker, Inc., New York (2001); Antiperspirants and Deodorants, Editors—K. Laden and C. Felger, Cosmetic Science and Technology Series/Volume 7, Marcel Dekker, Inc., New York (1988); and Antiperspirants and Deodorants, 2nd Edition, Editor—K. Laden, Cosmetic Science and Technology Series/Volume 20, Marcel Dekker, Inc., New York (1999), each incorporated herein by reference in its entirety for all purposes.

The claimed antiperspirant composition may be provided in various forms including, but not limited to, aerosol, gels, creams, solid stick, semi-solid stick, powder, liquid, emulsion, suspension, dispersion and the like. Preferably, the form is either a stick, semi-solid stick, liquid or powder. More preferably the form is either a liquid or a powder.

Also, the particular form of the claimed antiperspirant composition is preferably provided in a suitable container such as an aerosol can (aerosol), tube or container with porous cap (gel), roll-on or bottle (liquid), container with open end (stick, pad or wipe) and the like—whatever is suitable for the particular exemplary form. Of course, the claimed invention is claimed as the composition itself and does not require that it be dispensed or provided in a suitable container to fall within the scope of the appended claims.

Given the exemplary amounts of the foregoing components listed, it should be noted that the combination of the ingredients of the claimed antiperspirant composition should be sufficient to increase the "first ratio" by at least about (1) 0.5, (2) 0.8, (3) 1, (4) 1.5, (5) 2, (6) 2.5, (7) 3, (8) 3.5, (9) 4, or (10) 4.5, respectively, when compared to that of a comparable composition without both the betaine and calcium salt components. Likewise, it is desired that the ingredients of the claimed antiperspirant composition should be sufficient to increase the "first ratio" (11) from about 0.5 to about 10, (12) from about 0.8 to about 8, (13) from about 1 to about 6, or (14) from about 1 to about 4, respectively, when compared to that of a comparable composition without both the betaine and calcium salt components.

Given the exemplary amounts of the foregoing components listed, it should be noted that the combination of the ingredients of the claimed antiperspirant composition should be sufficient to decrease the "second ratio" to less than about (1) 0.4, (2) 0.35, (3) 0.3, (4) 0.25, (5) 0.2, (6) 0.15, (7) 0.1, (8) 0.05, (9) 0.04, (10) 0.03, (11) 0.02, or (12) 0.01, respectively, when compared to that of a comparable composition without both the betaine and calcium salt components. Preferably, according to one embodiment, the claimed antiperspirant has a "second ratio" of 0.

Given the exemplary amounts of the foregoing components listed, it should be noted that the combination of the ingredients of the claimed antiperspirant composition should be sufficient to increase the "27Al NMR peak intensity at 63.5 ppm" by at least about (1) 20% (note peak intensity is not weight %), (2) 100%, (3) 200%, (4) 300%, (5) 400%, (6) 500%, (7) 600%, (8) 700%, (9) 800, or (10) 900, respectively, when compared to that of a comparable composition without both the betaine and calcium salt components.

ADDITIONAL EXAMPLES

Analytical Method for Examples a. Size Exclusion Chromatography ("SEC"):

Size exclusion chromatography ("SEC") or gel permeation chromatography ("GPC") are methods frequently used for obtaining information on polymer distribution in antiperspirant salt solutions. With appropriate chromatographic columns, at least five distinctive groups of polymer species can be detected in a ZAG, appearing in a chromatogram as peaks 1, 2, 3, 4 and a peak known as "5,6". Peak 1 is the larger zirconium species (greater than 60 Angstroms). Peaks 2 and 3 are larger aluminum species. Peak 4 is the smaller aluminum species (aluminum oligomers) and has been correlated with enhanced efficacy for both ACH and ZAG salts. Peak 5,6 is the smallest aluminum species. The relative retention time ("Kd") for each of these peaks varies depending on the experimental conditions. This method is also applicable to ZAB (zirconium-aluminum-betaine) salts. Data for Table A was obtained using the SEC method described in an issued patent owned by the same company as a this case, U.S. Pat. No. 6,066,314, incorporate by reference as to the test method described therein.

b. NMR Measurements:Sample Preparation:

Samples were prepared by diluting 0.2 ml product in 0.8 ml D2O to yield solution at concentrations of 7.0%. Samples were weighted and dissolved in D2O to produce 7.0% active solutions. A blank sample, using same type of NMR tube and only contain D2O, was also prepared to obtained the background signal from the NMR probe and test tubes. All NMR measurements were preformed immediately after the samples were prepared.

c. NMR Experimental Conditions:

Bruker Avance DMX500 NMR spectrometer with a inverse broadband 5 mm probe was used for all NMR measurements, which operated at the frequency of 130.323 MHz for 27Al. Single pulse with CYCLOPS was used during all experiments with recycle delay at 3 second, RF pulse width at 17 □s at 0 db RF attenuation (which is 90 degree pulse). Total number of scans for each data set is 1024, and the 64K data points (correspond to 1 second acquisition time) were acquired for each FID data set. The spectral width is 32679 Hz, which is equivalent to 250 ppm. The dewell time is 20 □s, which is the delay time between the end of RF pulse and the starting point of data acquisition. The magnetic field was locked by deuteratied water in all the samples. All NMR experiments were carried out at room temperature (21 C) without specific temperature control. A blank NMR spectrum of the background was also recorded with exactly the same parameters.

d. NMR Data Analysis:

All NMR FID data were processed with same parameters: FFT data size was 64K, and an exponential window function (LB=5 Hz) was applied before FFT to improve signal to noise ratio. Since the blank spectrum showed a broad background 27Al signal at 72 ppm, it were subtracted from all spectra for real samples to produce spectra without background signal.

The subtractions were performed in spectral domain, where the exact same processing parameters were used for sample data set and the background signal, especially the phase parameters. Automatic baseline corrections were also performed on all data sets after background correction. Since there were severe signal overlap from −20 to 40 ppm, line shape deconvolutions were performed on all data sets to obtain peak position, line width, and integration. Initial conditions were set with four resonance signals in this region, usually several runs at different initial conditions were necessary to obtain good deconvolution results. The deconvolution function in Bruker X-WinNMR (version 2.5) was used, and a mixed line shape of Lorentzian and Gaussian (low percentage) was used for all data sets.

Antiperspirant Salts with Betaine and Calcium

Example 1

A solution was made by mixing 4 gm of CaCl2 and 2 gm of betaine anhydrous with 20 gm (USP weight) ACH powder (Reheis CHLORHYDROL®) in water, making the total weight 100 gm. The solution was then divided into two parts: One part was aged at 70° C. overnight, and the second part was kept at room temperature for the same time period. The sample solutions were analyzed afterwards by the SEC method described earlier, as well as the ACH solution as control. As shown in Table 1, after being aged, the ACH sample with CaCl2 and betaine showed significant increase in Peak-4/Peak-3 ratio, especially at higher temperature.

TABLE 1

SEC peak distribution (RI Detector)

| Sample | Peak-4/Peak-3 |
|---|---|
| ACH (20%, USP) | 0.244 |
| ACH (20%, USP) + CaCl$_2$ (4%) + betaine (2%) (Aged at 70° C., overnight) | 1.43 |
| ACH (20%, USP) + CaCl$_2$ (4%) + betaine (2%) (Aged at RT, overnight) | 0.65 |

NMR analysis also indicated that the peak-4 species created by mixing ACH, CaCl$_2$, and betaine was very close to that in Reach-101, a thermally activated ACH with Al 13-mers in peak-4. The strength of NMR peak at 63.5 ppm representing the Al tetrahedron in the center of Al 13-mer increased from 0.388 to 1.0854 after the regular ACH was mixed with CaCl$_2$ and betaine and then aged, suggesting the enhancement of Al 13-mers by this process.

TABLE 2

Relative peak strength of $^{27}$Al NMR

| Sample | 63.5 ppm |
|---|---|
| ACH | 0.388 |
| Activated ACH, Reach-101 | 1.000 |
| ACH (20%, USP) + CaCl$_2$ (4%) + betaine (2%) (Aged at 70° C., overnight) | 1.085 |

Example 2

A solution was made by mixing 5 gm of CaCl2 and 2 gm of betaine anhydrous with 20 gm (USP weight) ACH powder (Reheis CHLORHYDROL®) in water, making the total weight 100 gm. The solution was aged at room temperature, and then analyzed at different periods of time by the SEC method described earlier, with the ACH sample solution as control. As shown in Table 2, Peak-4 kept going up over time indicated by the increasing Peak-4/Peak-3 ratio.

TABLE 2

SEC peak distribution (RI Detector)

| Sample | Peak-4/Peak-3 |
|---|---|
| ACH (20%, USP) | 0.24 |
| ACH (20%, USP) + CaCl$_2$ (5%) + betaine (2%) (Aged at RT, 1 week) | 1.49 |
| ACH (20%, USP) + CaCl$_2$ (5%) + betaine (2%) (Aged at RT, 1 months) | 1.72 |
| ACH (20%, USP) + CaCl$_2$ (5%) + betaine (2%) (Aged at RT, 2 months) | 2.35 |
| ACH (20%, USP) + CaCl$_2$ (5%) + betaine (2%) (Aged at RT, 6 months) | 3.09 |

Example 3

Different amount of CaCl2 and betaine anhydrous were added into AZP-955 solution, a glycine free Al—Zr-chlorohydrex made by Reheis, Inc., to form four sample solutions with concentrations of the ingredients shown in Table 3. The sample solutions were aged at 45° C. a week afterwards, and then checked by SEC for polymer size distribution profile. Table 3 exhibits the peak ratios of peak-1/(peak-2+peak-3+peak-4+peak-5) and Peak-4/peak-3, measuring large zirconium polymer species and aluminum 13-mers, or peak-4 species, respectively.

Obviously, both betaine and Ca++ ions were needed to boost peak-4 species, or aluminum 13-mers, in the sample solutions: The samples with both showed considerable increase in peak-4/peak-3 ratio, while the one with only betaine or CaCl2 did not have any positive change in the ratio after being aged. Furthermore, dose response effect of CaCl2 was clearly demonstrated in this example: The sample with higher level of Ca++ (6.54% of CaCl2) presented a much higher peak-4/peak-3 ratio than the one with lower level of Ca++ (2.17% CaCl2).

The effect of betaine in stabilizing zirconium species was also demonstrated in this example: All the sample solutions with the presence of betaine showed detectable reduction in peak-1/(peak-2+peak-3+peak-4+peak-5) ratio, indicating small zirconium species being stabilized.

TABLE 3

SEC peak distribution (RI Detector)

| Sample | Peak-1/(P2 + P3 + P4 + P5) | Peak-4/Peak-3 |
|---|---|---|
| AZP-955 (18.9%) as control | 0.38 | 0.29 |
| AZP-955 (18.9%) + CaCl$_2$ (2.17%) + betaine (3.3%) | 0.26 | 0.85 |
| AZP-955 (18.9%) + CaCl$_2$ (6.54%) + betaine (3.3%) | 0.27 | 1.55 |
| AZP-955 (18.9%) + CaCl$_2$ (0%) + betaine (3.3%) | 0.23 | 0.25 |
| AZP-955 (18.9%) + CaCl$_2$ (2.17%) + betaine (0%) | 0.43 | 0.28 |

Example 4

Samples were made by adding CaCl2 and water into ZAB-317321-I, or ZAB-317321-II aqueous solution, the Reheis prepared Zr—Al-Chlorohydrex-betaine AP salt with betaine/zirconium molar ratio of 0.82, or 1.32 respectively, to come out with the solution samples with concentration of ingredients listed in table 4. The samples were then aged for a month at room temperature.

Table 4 presents the SEC results in peak ratios of peak-1/(peak-2+peak-3+peak-4+peak-5) and Peak-4/peak-3, clearly revealing the effect of combination of betaine and Ca++ on zirconium polymers and peak-4 species respectively. The samples with higher betaine level, betaine/zirconium of 1.23, exhibited lower peak ratios of peak-1/(peak-2+peak-3+peak-4+peak-5), suggesting more stabilized small zirconium species.

The trend was equally evident with regard to peak-4 species: The sample with the highest level of both Ca++ and betaine, 6.54% of CaCl2 and betaine/zirconium ratio of 1.23, showed the highest peak-4/peak-3 ratio of 1.73, whereas the ones of lower levels of betaine and zirconium revealed lower peak-4/peak-3 ratios accordingly.

In addition, this example further proved that if without Ca++, betaine alone would not boost peak-4 species. The two samples with different level of betaine, while without Ca++, exhibited identical peak-4/peak-3 ratios.

TABLE 4

SEC peak distribution (RI Detector)

| Sample | Peak-1/(P2 + P3 + P4 + P5) | Peak-4/Peak-3 |
|---|---|---|
| ZAB-317321-I (betaine/Zr = 0.82) - 19% solution | 0.17 | 0.27 |
| ZAB-317321-I (betaine/Zr = 0.82) - 19% solution + CaCl$_2$ (2.17%) | 0.17 | 0.57 |
| ZAB-317321-I (betaine/Zr = 0.82) - 19% solution + CaCl$_2$ (6.54%) | 0.17 | 0.75 |
| ZAB-317321-II (betaine/Zr = 1.23) - 19% solution | 0.03 | 0.27 |
| ZAB-317321-II (betaine/Zr = 1.23) - 19% solution + CaCl$_2$ (2.17%) | 0.03 | 0.94 |
| ZAB-317321-II (betaine/Zr = 1.23) - 19% solution + CaCl$_2$ (6.54%) | 0.03 | 1.73 |

Example 5

Dissolve 19.26 gm ZrOCl2.8H2O and 8.39 g betaine anhydrous in 30 gm of water to prepare an antiperspirant (AP) salt solution. After everything is dissolved, add ACH powder (22.65 g of Chlorhydrol from Reheis Chemical Co., Berkeley Heights, N.J.) and 12 gm of CaCl2.2H2O into the solution with additional water so that the total weight of the solution reaches 100 gm. Shake and/or stir the solution until the solution becomes clear.

Such 30% salt solution (anhydrous basis) will have the following composition:

| Al/Zr = 3.5 | Metal/Cl = 1.2 | betaine/Zr = 1.2 | Ca/betaine = 3.2 |
|---|---|---|---|
| Al: | 5.64% | 0.209 Mole | |
| Zr: | 5.45% | 0.0597 Mole | |
| Cl: | 7.95% | 0.224 Mole | |
| betaine: | 8.39% | 0.0716 Mole | |
| CaCl$_2$ | 9.06% | 0.082 Mole | |

Optionally, spray dry or freeze-dry the solution to make a powder sample.

Example 6

Dissolve 19.26 g ZrOCl2.8H2O in 49.6 gm of water and then add 5.36 g betaine anhydrous to prepare and AP salt solution. After everything is dissolved, add ACH powder (22.65 gm of Chlorhydrol from Reheis) and 12 gm of CaCl2.2H2O into the solution with additional DI water so that the total weight of the solution reaches 100 gm. Shake and/or stir the solution until it is clear.

Such 30% salt solution (anhydrous basis) will have the following composition:

| Al/Zr = 3.5 | Metal/Cl = 1.2 | betaine/Zr = 0.76 | Ca/betaine = 5.0 |
|---|---|---|---|
| Al: | 5.64% | 0.209 Mole | |
| Zr: | 5.45% | 0.0597 Mole | |
| Cl: | 7.95% | 0.224 Mole | |
| betaine: | 5.36% | 0.0457 Mole | |
| CaCl$_2$ | 9.06% | 0.082 Mole | |

Optionally, spray dry or freeze-dry the solution to make a powder sample.

Example 7

Dissolve 19.26 g of ZrOCl2.8H2O in 40 gm of distilled water and then add 9.68 g of betaine monohydrate to prepare an AP salt solution. After everything is dissolved, ad ACH powder (22.65 g of Chlorhydrol from Reheis) and 5 gm of CaCl2.2H2O to the solution with additional DI water so that the total weight of the solution reaches 100 gm. Shake and/or stir the solution until a 30% salt solution (anhydrous basis) is obtained.

Such 30% salt solution (anhydrous basis) will have the following composition:

| Al/Zr = 3.5 | M/Cl = 1.2 | betaine/Zr = 1.2 | Ca/betaine = 1.32 |
|---|---|---|---|
| Al: | 5.64% | 0.209 Mole | |
| Zr: | 5.45% | 0.0597 Mole | |
| Cl: | 7.95% | 0.224 Mole | |
| Betaine: | 8.39% | 0.0716 Mole | |
| CaCl$_2$ | 3.77% | 0.034 Mole | |

Spray dry or freeze-dry the solution to make a powder sample if needed.

Example 8

Dissolve 100 gm Zr(OH)2CO3.ZrO2 in 400 gm of distilled water and then add 100 gm of betaine hydrochloride to prepare an AP salt solution. After every thing is dissolved, add ACH (226.5 gm of Chlorhydrol from Reheis) and 50 gm of CaCl2.2H2O to the solution, as well as some additional water to make the total solution of 1000 gm. Shake and/or stir the solution of 24% (anhydrous) until it is clear. Such 24% salt solution (anhydrous basis) will have the following composition:

| Al/Zr = 3.2 | Metal/Cl = 1.6 | betaine/Zr = 1.9 |
|---|---|---|
| Al: | 5.64% | 2.09 |
| Zr: | 5.92% | 0.649 |

-continued

| Al/Zr = 3.2 | Metal/Cl = 1.6 | betaine/Zr = 1.9 |
|---|---|---|
| Cl: | 6.10% | 1.72 |
| betaine: | 7.63% | 0.65 |
| CaCl$_2$ | 1.36% | 0.123 Mole |

Spray dry or freeze-dry the solution to make a powder sample if needed.

Example 9

Dissolve 60 gm Zr(OH)2CO3.ZrO2 in 101 gm of HCl solution (37%) and 400 gm of distilled water and then add 100 gm of betaine hydrochloride to prepare an AP salt solution. After every thing is dissolved, add ACH (226.5 gm of Chlorhydrol from Reheis) and 50 gm of CaCl2.2H2O to the solution, as well as some water to make the total solution 1000 gm. Shake and/or stir the solution of 26.3% (anhydrous) until it is clear. Such 26.3% salt solution (anhydrous basis) will have the following composition:

| Al/Zr = 5.4 | Metal/Cl = 1.2 | betaine/Zr = 1.9 |
|---|---|---|
| Al: | 5.64% | 2.09 |
| Zr: | 3.55% | 0.389 |
| Cl: | 7.32% | 2.06 |
| betaine: | 7.63% | 0.65 |
| CaCl$_2$: | 3.77% | 0.34 |

Spray dry or freeze-dry the solution to make a powder sample if needed.

Example 10

Dissolve 118.1 gm ZrCO3.7.56H2O in 101 gm of HCl solution (37%) and 400 gm of distilled water and then add 100 gm of betaine hydrochloride to prepare an AP salt solution. After every thing is dissolved, add ACH (226.5 gm of Chlorhydrol from Reheis) and 50 gm of CaCl2.2H2O to the solution, as well as some water to make the total solution 1000 gm. Shake and/or stir the solution of 26.3% (anhydrous) until it is clear. Such 26.3% salt solution (anhydrous basis) will have the following composition:

| Al/Zr = 5.4 | Metal/Cl = 1.2 | betaine/Zr = 1.9 |
|---|---|---|
| Al: | 5.64% | 2.09 |
| Zr: | 3.55% | 0.389 |
| Cl: | 7.32% | 2.06 |
| betaine: | 7.63% | 0.65 |
| CaCl$_2$: | 3.77% | 0.34 |

Spray dry or freeze-dry the solution to make a powder sample if needed.

Example 11

Dissolve 118.1 gm ZrOCO3.7.56H2O in 73.3 gm of HCl solution (37%) and 400 gm of distilled water and then add 100 gm of betaine hydrochloride. After every thing is dissolved, add ACH (226.5 gm of Chlorhydrol from Reheis) and 50 gm of CaCl2.2H2O to the solution, as well as some water to make the total solution 1000 gm. Shake or stir the 26.3% (anhydrous) solution until it is clear. Such 26.3% salt solution (anhydrous basis) will have the following composition:

| Al/Zr = 5.4 | Metal/Cl = 1.4 | betaine/Zr = 1.9 |
|---|---|---|
| Al: | 5.64% | 2.09 |
| Zr: | 3.55% | 0.389 |
| Cl: | 6.27% | 1.77 |
| betaine: | 7.63% | 0.65 |
| CaCl$_2$: | 3.77% | 0.34 |

Spray dry or freeze-dry the solution to make a powder sample if needed.

Example 12

Dissolve 30 g ADCH in 54 gm of DI water to prepare a solution of aluminum dichlorohydrex (ADCH, Westchlor 100, 38%). After the solution is mixed and becomes clear, add 8 gm of anhydrous betaine and 8 gm of CaCl2.2H2O. Mix the solution at room temperature until clear. The final solution will have a betaine/aluminum molar ratio of 0.61 and a Ca/betaine ratio of 1.41.

Example 13

Mix a 31% solution of zirconium oxychloride (ZrOCl2) with 8 gm anhydrous betaine and 12 gm of CaCl2.2H2O and stir at room temperature until clear. The final solution will have a betaine/zirconium molar ratio of 0.43, and a Ca/betaine ratio of 2.11, and a zirconium/chloride ratio of 0.50.

Example 14

An aqueous solution was made a by adding 1.5 gm CaCl2.2H2O, 7.0 gm of ethanol (200 proof) and 6.8 gm of distilled water into a ZAB (Zirconium-Aluminum-Chlorohydrex with betaine) aqueous solution (29.5% anhydrous, betaine/Zr=1.2, M/Cl=1.1) prepared by Reheis Co. The solution was then stirred well and ready to be used in all solution based formulas.

What is claimed is:

1. An antiperspirant composition comprising:
   (a) an antiperspirant salt selected from the group consisting of an aluminum antiperspirant salt, an aluminum-zirconium antiperspirant salt, and a mixture thereof, wherein the aluminum antiperspirant salt is a least one salt selected from aluminum chlorohydrate, aluminum dichlorohydrate, aluminum sesquichlorohydrate, aluminum chlorohydrex propylene glycol, aluminum dichlorohydrex propylene glycol, aluminum sesquichlorohydrex propylene glycol, aluminum chlorohydrex polyethylene glycol, aluminum dichlorohydrex polyethylene glycol, and aluminum sesquichlorohydrex polyethylene glycol;
   (b) a trimethylglycine component selected from the group consisting of trimethylglycine, trimethylglycine hydrochloride, and a mixture thereof; and
   (c) a calcium salt
   wherein said calcium salt component (c) together with said trimethylglycine component (b) is provided in an amount sufficient to increase a first ratio of an HPLC peak 4 area to peak 3 area, said peak 4 area being proportional to a first amount of a polymer of said antiperspirant salt and said peak 3 area being proportional to a second amount of a larger polymer of said antiperspirant salt.

2. The composition of claim 1, further comprising water.

3. The composition of claim 1, wherein said first ratio is increased to at least 0.5.

4. The composition of claim 1, wherein said first ratio is increased to at least 1.

5. The composition of claim 1, wherein said first ratio is increased to at least 2.

6. The composition of claim 1, wherein said first ratio is increased to at least 3.

7. The antiperspirant composition of claim 1, wherein said first ratio is increased to at least 4.

8. The composition of claim 1, wherein said antiperspirant salt is said aluminum-zirconium antiperspirant salt, wherein said calcium salt component (c) together with said trimethylglycine component (b) is provided in an amount sufficient to decrease a second ratio of the peak area of HPLC peak 1 to a sum of the peak areas of HPLC peaks 2, 3, 4 and 5.

9. The composition of claim 8, wherein said second ratio is decreased to less than 0.4.

10. The composition of claim 9, wherein said second ratio is decreased to less than 0.3.

11. The composition of claim 10, wherein said second ratio is decreased to less than 0.2.

12. The composition of claim 11, wherein said second ratio is decreased to less than 0.1.

13. The composition of claim 12, wherein said second ratio is 0.

14. The composition of claim 1, wherein said component (b) is provided in an amount from about 0.5 to about 40 wt % based on a total weight of said antiperspirant composition.

15. The composition of claim 1, wherein said component (c) is provided in an amount from about 0.2 to about 80 wt % based on a total weight of said antiperspirant composition.

16. The composition of claim 1, wherein said calcium salt is selected from the group consisting of calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide and mixtures thereof.

17. The composition of claim 1, wherein said component (a) is provided in an amount from about 5% by weight to about 85% by weight based on a total weight of said antiperspirant composition.

18. The composition of claim 1, wherein said calcium salt component (c) together with said trimethylglycine component (b) is provided in an amount sufficient to increase an $^{27}$Al NMR peak intensity at 63.5 ppm.

19. The composition of claim 18 wherein said increase in said $^{27}$Al NMR peak intensity is at least 20%.

20. The composition of claim 19 wherein said increase in said $^{27}$Al NMR peak intensity is at least 100%.

21. The composition of claim 20 wherein said increase in said $^{27}$Al NMR peak intensity is at least 300%.

22. The composition of claim 21 wherein said increase in said $^{27}$Al NMR peak intensity is at least 500%.

23. The composition of claim 22 wherein said increase in said $^{27}$Al NMR peak intensity is at least 700%.

24. The composition of claim 23 wherein said increase in said $^{27}$Al NMR peak intensity is at least 900%.

25. The composition of claim 1, wherein the antiperspirant salt is in the range from 5-85 weight % based on a total weight of said antiperspirant composition.

26. The composition of claim 25, wherein the antiperspirant salt is in the range from about 10-60 weight % based on the total weight of said antiperspirant composition.

27. The composition of claim 26, wherein the antiperspirant salt is in the range from about 15-35 weight % based on the total weight of said antiperspirant composition.

28. The composition of claim 1, wherein the trimethylglycine component (b) is present in an amount of at least 0.1 weight % based on a total weight of said composition.

29. The composition of claim 28, wherein the trimethylglycine component (b) is in the range from about 0.5-40 weight % based on the total weight of said composition.

30. The composition of claim 29, wherein the trimethylglycine component (b) is in the range from about 2.0-30 weight % based on a total weight of said composition.

31. The composition of claim 30, wherein the trimethylglycine component (b) is in the range from about 4.0-20 weight % based on the total weight of said composition.

32. The composition of claim 1, wherein the calcium salt component (c) is present in an amount of at least 0.1 weight % based on a total weight of said composition.

33. The composition of claim 32, wherein the calcium salt component (c) is in the range from about 0.2-80 weight % based on the total weight of said composition.

34. The composition of claim 33, wherein the calcium salt component (c) is in the range from about 0.4-40 weight % based on the total weight of said composition.

35. The composition of claim 34, wherein the calcium salt component (c) is in the range from about 0.5-10 weight % based on the total weight of said composition.

36. The composition of claim 1, further comprising a water soluble alcohol.

37. The composition of claim 36, wherein said water soluble alcohol is a $C_2$-$C_8$ alcohol.

38. The antiperspirant composition of claim 37, where said water soluble alcohol is ethanol.

39. The composition of claim 36, wherein said water soluble alcohol is selected from the group consisting of glycol, propylene glycol, dipropylene glycol, tripropylene glycol and mixtures thereof.

40. The composition of claim 1, further comprising glycine in an amount from about 0-40 weight % based on a total weight of said composition.

41. The composition of claim 40, wherein said glycine is provided in an amount from about 1-30 weight % based on the total weight of said composition.

42. The composition of claim 41, wherein said glycine is provided in an amount from about 2-20 weight % based on the total weight of said composition.

43. The composition of claim 42, wherein said glycine is provided in an amount from about 8-10% based on the total weight of said composition.

44. The composition of claim 1, wherein the composition is in the form of a powder, a liquid, a gel, or a solid.

* * * * *